(12) United States Patent
Kroll-Orywahl et al.

(10) Patent No.: US 9,751,243 B2
(45) Date of Patent: Sep. 5, 2017

(54) ORTHOPAEDIC MOULDING ARRANGEMENT AND METHOD FOR PRODUCING AN ORTHOPAEDIC MOULDING

(75) Inventors: Olaf Kroll-Orywahl, Göttingen (DE); Gordon Siewert, Göttingen (DE); Michael Nolte, Seeburg (DE); Michael Ottleben, Kalefeld (DE)

(73) Assignee: OTTO BOCK HEALTHCARE GMBH, Duderstadt (DE)

( * ) Notice: Subject to any disclaimer, the term of this patent is extended or adjusted under 35 U.S.C. 154(b) by 175 days.

(21) Appl. No.: 13/816,129

(22) PCT Filed: Aug. 8, 2011

(86) PCT No.: PCT/EP2011/003959
§ 371 (c)(1),
(2), (4) Date: Apr. 15, 2013

(87) PCT Pub. No.: WO2012/019744
PCT Pub. Date: Feb. 16, 2012

(65) Prior Publication Data
US 2013/0193610 A1    Aug. 1, 2013

(30) Foreign Application Priority Data

Aug. 9, 2010   (DE) .................. 10 2010 033 809

(51) Int. Cl.
*B29C 65/34*   (2006.01)
*A61F 5/01*    (2006.01)
(Continued)

(52) U.S. Cl.
CPC ............... *B29C 43/18* (2013.01); *A61F 5/01* (2013.01); *A61F 5/02* (2013.01); *A61F 5/058* (2013.01);
(Continued)

(58) Field of Classification Search
CPC ............ B29C 65/3456; B29C 65/3452; B29C 65/3448; B29C 65/3444; B29C 43/12;
(Continued)

(56) References Cited

U.S. PATENT DOCUMENTS 3,326,211 A    6/1967  Logue et al.
4,560,428 A *  12/1985 Sherrick et al. ................ 156/94
(Continued)

FOREIGN PATENT DOCUMENTS

CN    1159156 A    9/1997
CN    2413659 Y    1/2001
(Continued)

OTHER PUBLICATIONS

International Search Report for International Application No. PCT/EP2011/003959, mailed Sep. 19, 2012.

*Primary Examiner* — William Bell
(74) *Attorney, Agent, or Firm* — Holland & Hart

(57) ABSTRACT

A method for producing a molding, the shape of which is adapted to an initial mold, in which method a plurality of layers are deformably placed on top of one another such that the layers can be joined to each other by heat. The layers are deformed by being pressed onto the initial mold and in order to join the layers. Heat is applied in the deformed state. In the arrangement made of layers, at least one converter element is introduced that transforms supplied energy into heat energy and with which at least parts of the layers are heated to join the layers.

9 Claims, 2 Drawing Sheets

(51) Int. Cl.

| | |
|---|---|
| *B29C 43/18* | (2006.01) |
| *A61F 5/02* | (2006.01) |
| *A61F 5/058* | (2006.01) |
| *A61F 13/04* | (2006.01) |
| *B29C 51/14* | (2006.01) |
| *B29C 51/42* | (2006.01) |
| *B29C 65/36* | (2006.01) |
| *B29C 65/00* | (2006.01) |
| *A61F 13/00* | (2006.01) |
| *B29L 31/00* | (2006.01) |

(52) U.S. Cl.
CPC ............ *A61F 13/04* (2013.01); *B29C 51/145* (2013.01); *B29C 51/421* (2013.01); *B29C 65/342* (2013.01); *B29C 65/362* (2013.01); *B29C 66/1122* (2013.01); *B29C 66/5326* (2013.01); *B29C 66/73921* (2013.01); *B29C 66/81455* (2013.01); *A61F 2013/00625* (2013.01); *A61F 2013/00629* (2013.01); *B29C 65/3468* (2013.01); *B29C 65/3476* (2013.01); *B29C 65/3668* (2013.01); *B29C 66/71* (2013.01); *B29C 66/729* (2013.01); *B29C 66/7292* (2013.01); *B29C 66/73941* (2013.01); *B29L 2031/7532* (2013.01)

(58) Field of Classification Search
CPC ..... B29C 51/36; B29C 35/0272; B29C 65/34; B29C 65/7855; A61F 2013/00625; A61F 5/05841; A61F 5/05833; A61F 2013/00629; B29L 2031/7532
See application file for complete search history.

(56) References Cited

U.S. PATENT DOCUMENTS

| | | | |
|---|---|---|---|
| 4,657,003 A | | 4/1987 | Wirtz |
| 4,963,215 A | * | 10/1990 | Ayers .................... B29C 70/345 156/286 |
| 5,016,624 A | | 5/1991 | Garrett et al. |
| 6,129,695 A | * | 10/2000 | Peters et al. .................... 602/62 |
| 6,312,247 B1 | * | 11/2001 | Kassuelke ............ B29C 70/342 156/382 |
| 2001/0031935 A1 | * | 10/2001 | Andersen ........................ 602/23 |
| 2002/0177797 A1 | | 11/2002 | Henderson et al. |
| 2008/0319362 A1 | | 12/2008 | Joseph |
| 2009/0171356 A1 | * | 7/2009 | Klett ............................... 606/54 |

FOREIGN PATENT DOCUMENTS

| | | |
|---|---|---|
| EP | 0004829 A2 | 10/1979 |
| EP | 637280 B1 * | 9/1996 |
| GB | 698255 A | 10/1953 |
| GB | 2349822 A | 11/2000 |
| WO | 2008092443 | 8/2008 |

* cited by examiner

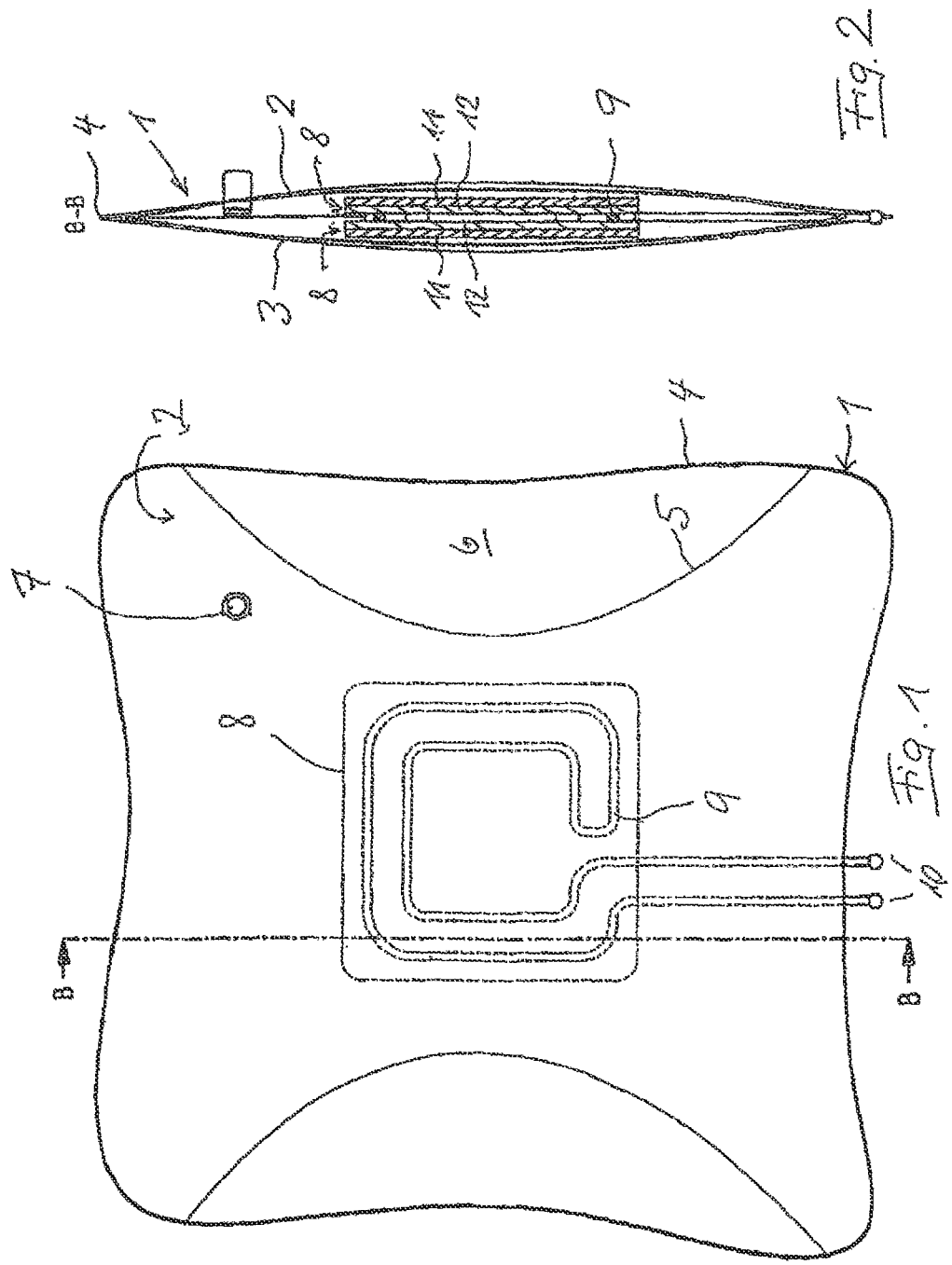

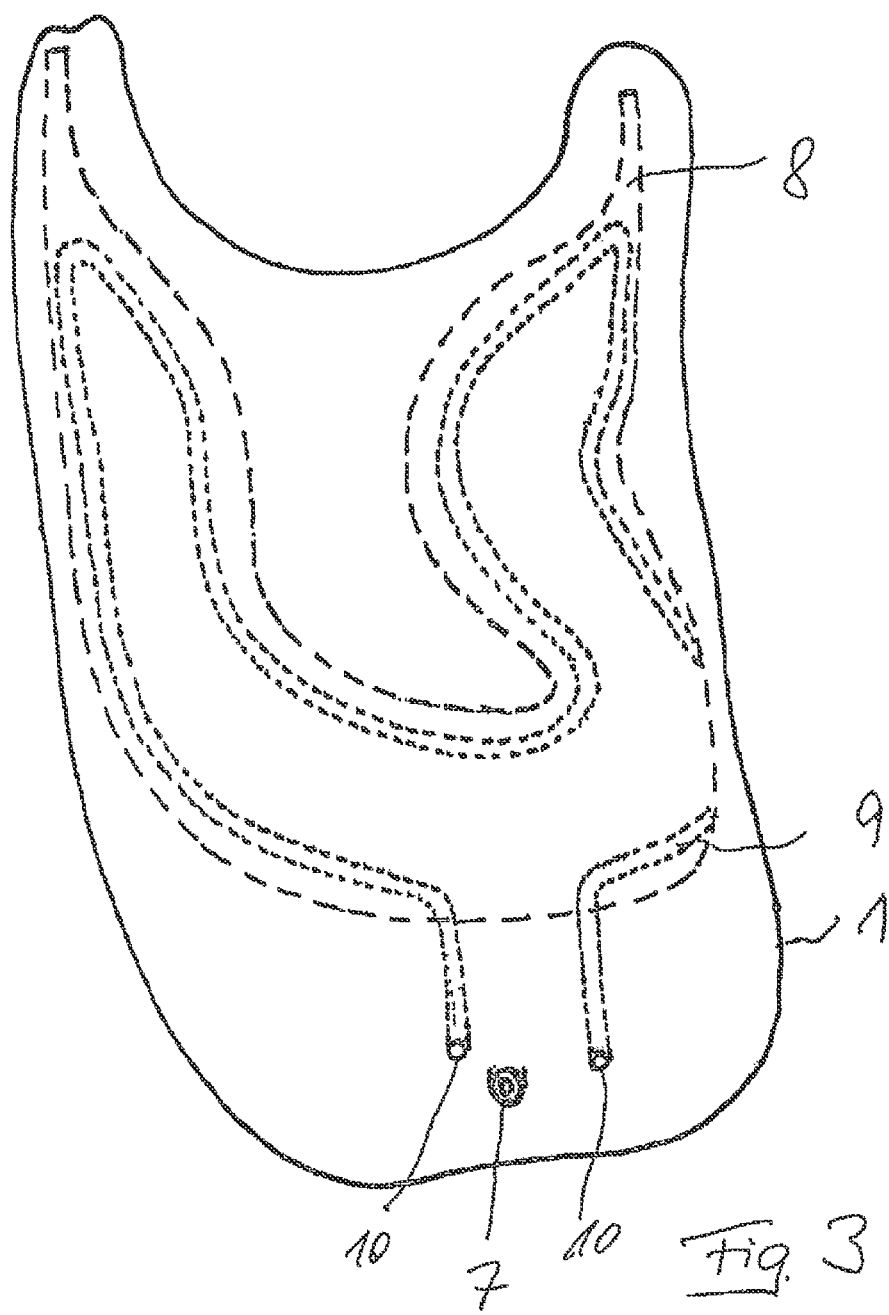

ORTHOPAEDIC MOULDING ARRANGEMENT AND METHOD FOR PRODUCING AN ORTHOPAEDIC MOULDING

TECHNICAL FIELD

The invention refers to a method for producing a moulding, the shape of which is adapted to an initial mould, in which method a plurality of layers are deformably placed on top of one another such that said layers can be joined to each other by heat, the layers are deformed by being pressed onto the initial mould and in order to join the layers, heat is applied in the deformed state.

The invention also refers to an orthopedic moulding arrangement with layers placed on top of one another, which can be joined to each other by heat after having been draped over a body shape for adaptation.

BACKGROUND

Orthopedic equipment, such as prostheses and orthoses require moulding with which the the equipment can be joined to the body. Alongside standard mouldings in various sizes, mouldings which have been specially adapted to the relevant bodies of the patients are often used. The production of these specially adapted mouldings occurs conventionally by means of an impression of the relevant body using a suitable material, such as plaster. This mould is made by an orthopedic technician who regularly sends the mould to a production company for orthopedic equipment, in order to have a piece of orthopedic equipment made to a specially adapted moulding, particularly an orthosis. For the moulding of an orthosis it is required, for example, to produce a positive mould with the plaster impression, which corresponds to the shape of the body part. With this mould, the design of the real orthopedic moulding is made. This process is not only time-consuming, but also requires the production of moulds which are only used once, which increases the price of the orthopedic equipment.

In WO 2008/092443 it is described that an orthopedic moulding in its finished form is arranged directly onto the body of the patient by providing the layers joined to each other with a plastic deformable insert which holds the deformation caused by the adaptation (draping) on the relative body part until the layers are joined by the hardening of a binding material. The production of the moulding must occur immediately after the impression, i.e. regularly at the orthopedic technician. This causes considerable restrictions on the production of the orthopedic equipment, which in many cases occurs in a specialized production company that has specialized production devices and testing facilities.

In US 2002/0177797 A1 orthopedic arrangements are described which comprise the support elements, which can be hardened, that can be adapted to a body part of the patient. These flat elements are impregnated in the middle part with a material that can be hardened, whilst the edge is free of this material. Following the adaptation to the body of the patient the element is hardened in the conventional way.

In US 2008/0319362 A1 a system is described for immobilizing and supporting of a body part where an in situ hardening should be explicitly avoided.

The U.S. Pat. No. 6,129,695 discloses joint protectors, such as those worn by athletes, for example. These sorts of protectors are provided with cushions or foam pads, for example, in order to produce a better protective effect. Should the various components of this sort of joint protector be sewn together, the wearer can experience irritation caused by the seams. In order to prevent this, it is suggested to join the various parts to each other using a thermoplastic material which is melted to join the parts. This occurs during the production of the protector by means of a heat electrode which is pressed onto the materials to be joined.

In GB 2 349 822 a splint is described with which the body parts can be splinted and immobilized. This comprises a case that is filled with a thermoplastic material. To adapt the splint to the body part, the material is heated and becomes fluid. Once it has cooled down, the splint remains in the shape adapted to the body part.

The above invention therefore aims to enable the production of a moulding, the necessary dimensional stability of the moulding being achieved easily and with little effort during or immediately after the moulding process of the initial mould.

To solve this aim, a process according to the invention like that mentioned at the beginning is characterized by the fact that, in the arrangement made of layers, at least one converter element is introduced that transforms supplied energy into heat energy and with which at least parts of the layers are heated to join the layers.

Accordingly, to solve the identified aim an orthopedic moulding arrangement according to the invention like that mentioned at the beginning is characterized by the fact that in the arrangement made of layers at least one converter element is introduced that transforms supplied energy into heat energy and with which at least parts of the layers are connected.

According to the invention it is thus intended that the layers joined to each other under the influence of heat are deformed (draped) by adapting them to the initial mould, especially to the body shape, and that the layers are joined to each other following deformation by supplying energy to the converter element. This energy supply creates the heat required to join the layers to each other.

A simple converter element is a heating conductor which has been introduced in the layer arrangement that can preferably be arranged between at least two layers. The connectors of this heating conductor are then led out of the layer arrangement. By means of a current through the heating conductor, the heat required to join the layers to each other can be generated.

In another embodiment, an arrangement that absorbs microwaves can be inserted into the layer arrangement, which can be heated very quickly by a short exposure to microwaves and thus generates the heat required to join the layers to each other. Moreover, the converter elements can be formed by electric conductors that are heated by electromagnetic fields created by induction coils. In this case, it is not necessary to lead the connectors out of the layer arrangement. Of course, other converter elements and ways to energize the converter elements are deployable, to which the energy can be supplied in a selective way. Alongside high frequency energy, the supply of, for example, ultrasonic energy comes into question for the generation of the necessary heat. It is essential for the invention that the heat is generated in the area around the converter elements and not in the layer material itself. These should at most be only marginally heated by the energy supply, and obtain the energy required for joining from the heated converter elements.

In a preferred implementation of the above invention, the joining of the layers is only temporarily produced, especially in order to be able to transport the mould taken from the body part safely to the production company for the orthopedic equipment. The joining of the layers is so stable that the mould taken remains intact during transportation to the production company. However, in this case it is not stable enough to withstand the loads during use of the orthopedic equipment, such as orthoses. Accordingly, a permanent joining of the layers does not take place in this case until it reaches the production company for orthopedic equipment. As a result, it is sufficient for this type of implementation that the joining of the layers only occurs locally, for example only in close proximity of a heating wire or a heating strip. For this purpose, joining the layers across the entire surface is neither required nor practical.

The joining that is carried out between the layers by the supply of heat can occur by means of a thermosetting material or a thermoplastic material. With a thermosetting material, the hardening occurs by means of a chemical transformation at higher temperatures. Here, the joining is usually permanently fixed. The joining with a thermoplastic material is preferable. The layers themselves can then be made from a thermoplastic material or be coated with a thermoplastic material, the layers still being separated from each other. The supply of heat then leads to a softening of the thermoplastic material, which causes the layers within the vicinity of the fluid thermoplastic material to join together when the thermoplastic material solidifies after cooling down. The same effect can be achieved by placing a thermoplastic intermediate layer in between the layers, for example in the form of a thermoplastic foil.

In a preferred embodiment, the layers are fiber layers, preferably fabric layers. This means that fiber layers impregnated with thermoplastic material, so-called prepregs, can be implemented. Furthermore it is possible to use fiber layers with fibers that have a fiber core which is coated with a thermoplastic casing. With a suitable control of the influence of heat, uncoated thermoplastic fibers can also be used. In this case it is advantageous if only the surface of the fibers is melted under the influence of heat.

For the retention of the deformation of the layers generated by pressing them against the body part, the layers can be arranged in a gas-proof casing in a manner known, which can be evacuated before and especially after deformation. The formation of a vacuum creates a manageable layer pack that is dimensionally stable against low loads. This evacuated layer pack can thus be removed from the body part and then the joining between the layers according to the invention can be produced. In this way, by using only locally arranged converter elements, such as with a few turns of a heating wire, it is possible to produce such a stable joining between the layers that the moulding produced can be transported so that it remains dimensionally stable, even if the layer is not (or no longer) situated in a vacuum.

However, a permanent joining of the layers according to the invention also is not to be ruled out if a correspondingly extensive application of heat on the layers is guaranteed, resulting in an extensive joining between the layers.

BRIEF DESCRIPTION OF THE DRAWINGS

With the aid of a drawing of an embodiment of the present invention will be explained in more detail. It shows:

FIG. 1 a schematic depiction of a moulding arrangement for the production of a moulding specially adapted to a body part;

FIG. 2 a cut along the line B-B in FIG. 1;

FIG. 3 a schematic view of a moulding adapted to a body part.

DETAILED DESCRIPTION

FIG. 1 shows the outline of a casing 1 as a flat foil bag that is closed on all sides. The casing is made from a gas-proof material and, in the flat state, consists of an upper side 2 and an underside 3, which are joined with each other in a surrounding edge 4. The surrounding edge 4 comprises a cushion-shaped outline in the depicted embodiment; in contrast to a basic square shape with rounded corners, the side edges taper in the middle. At the upper side 2 and the underside 3, the casing is provided with a curved tear line 5 on two opposing sides that stretches from one corner area to another corner area of the respective side edges. The tear line enables the defined bending of a restricted side area 6 by means of the curved tear line 5, in order to facilitate a three-dimensional deformation of the casing 1.

The upper side 2 of the casing 1 is provided with a valve 7, with which the inner area of the casing 1, restricted by the upper side 2 and the underside 3, can be evacuated using a connection to a vacuum pump. Between the upper side 2 and the underside 3 of the casing 1, two layers 8 are arranged in the middle of the casing 1, between which a heating conductor 9 is located as a converter element. In the depicted embodiment, the heating conductor 9 is shaped in two windings with several turnings, in order to cover the majority of a perimeter of the layers 8, which are essentially square-shaped. The heating conductor 9 is led out of the area around the layers 8 with two connectors 10, and also out of the casing 1 in a gas-proof mould.

FIG. 2 shows that the layers 8 each comprise an outer fiber layer 11 and an inner layer 12 made from a thermoplastic material, so that the heating conductor 9 has direct contact to the two layers 12 made from thermoplastic material.

The fiber layers 11 can be fabric layers made from any material, for example glass fibers, aramide fibers and/or glass fibers. The layer 12 can be made from any thermoplastic material that can be joined with the fiber layer 11, whether it is by welding, bonding, coating or the like.

The moulding arrangement depicted in FIG. 1 is pressed against a body part to be moulded as an initial mould, so that it lies completely and crease-free on the relative body outline. Air is then sucked out of the casing 1 via the valve 7, so that the layers 8 and the casing 1 form a vacuum pack in which they lie close to each other under pressure, whereby the layers 8 can no longer be deformed and move against each other. In this state, it is expedient to remove the shaped moulding arrangement from the body part 1 and connect a power source to the connectors 10 of the heating conductor. As a result, the layers 12 made from thermoplastic material of the layers 8 in the vicinity of the heating conductor 9 are welded together, as the current flow through the heating conductor 9 causes the area surrounding the heating conductor 9 to heat up, causing the thermoplastic material to melt locally and the melted thermoplastic material of the layers 12 opposite to join with each other, i.e. the layers 12 in the vicinity of the heating conductor 9 are thermally welded with each other. As the layers 12 are joined to the fiber layers 11, a secure bond occurs between the layers 8. The relative position of the layers 8 to each other—and also the shape of the moulding—are thus fixed by the welded joints created by means of the heating conductor 9.

FIG. 3 shows an embodiment of a moulding produced according to the invention after the the three-dimensional deformation, which is fixed by the evacuation of the casing 1 via the valve 7 and the welding of the layers 8 along the heating conductor 9. The connectors 10 are led out of the casing 1 in an undisturbed area and are cut off at the edge of the layers 8 for the production of the final mould.

In the depiction in FIG. 3 the layers 8, which form the moulding, are still situated in the casing 1. In this state, the moulded part can be transported in the protection of the casing 1, where it remains fixed in its shape by the welding of the layers 8. With the moulded layers 8, the desired orthopedic equipment can be produced following the removal of the casing 1 after transportation. For this purpose, the layers 8 can be permanently joined to each other, provided that only a temporary joining of the layers 8 was carried out with the heating conductor 9, as depicted in FIGS. 1 and 2. Of course the layers 8 can be supplemented with further layers during the production of the orthopedic equipment, which are adapted to the shape of the layers 8.

The invention therefore facilitates the production of orthopedic equipment specially adapted to a moulding of a relative body part without losing any shape and in an optimal distribution of tasks between an orthopedic technician and a specialist production company for orthopedic equipment. In a similar way, mouldings can also be produced from other initial moulds.

The invention claimed is:

1. A method for producing an orthopedic moulding, the shape of which is adapted to an initial mould, the method comprising:
    positioning a plurality of layers in a gas-proof casing;
    deformably placing the plurality of layers on top of one another while in the gas-proof casing such that said layers can be joined to each other by heat, the layers comprising a thermoplastic material or a coating comprising thermoplastic material, the layers are deformed by being pressed onto the initial mould and, in order to join the layers, heat is applied in the deformed state to melt the thermoplastic material, wherein in the arrangement made of layers, at least one converter element is introduced that transforms supplied energy into heat energy;
    solidifying by cooling down the thermoplastic material subsequent to applying heat, thereby only partially joining the deformed layers with a first load-withstanding stability;
    reheating and cooling the layers after a time interval, thereby permanently joining the deformed layers with a second load-withstanding stability, the second load-withstanding stability being greater than the first load-withstanding stability;
    creating a vacuum in the gas-proof casing before or after the layers are deformed.

2. The method according to claim 1, wherein the converter element is a heating conductor.

3. The method according to claim 1, wherein the plurality of layers comprise the thermoplastic material positioned between at least some of the layers.

4. A method for producing an orthopedic device, comprising:
    positioning a plurality of layers in a gas-proof casing, the plurality of layers comprising a thermoplastic material or a coating comprising thermoplastic material;
    positioning the plurality of layers on top of one another within an initial mould while in the gas-proof casing;
    positioning at least one converter between the plurality of layers;
    pressing the plurality of layers into the initial mould to deform the plurality of layers to match the shape of the initial mould;
    creating a vacuum in the gas-proof casing before or after the layers are deformed;
    applying heat to the plurality of layers in the deformed state with the at least one converter element to only partially join together the plurality of layers;
    subsequently cooling down the plurality of layer to provide a first load-withstanding stability;
    after cooling down the plurality of layers, heating the plurality of layers to permanently join the plurality of layers;
    cooling the permanently joined plurality of layers to provide a second load-withstanding stability, the second load-withstanding stability being greater than the first load-withstanding stability.

5. The method according to claim 4, wherein the at least one converter element comprises a heating conductor.

6. The method according to claim 4, wherein the heat from the at least one converter element used to partially join the plurality of layers only joins a portion of the plurality of layers adjacent to the at least one converter element, and the permanent joining of the deformed layers occurs after a time interval.

7. The method according to claim 4, wherein the plurality of layers comprise the thermoplastic material positioned between at least some of the layers.

8. The method according to claim 4, wherein the plurality of layers are joined by melting the thermoplastic material.

9. A method for producing an orthopedic device, comprising:
    positioning a plurality of layers in a gas-proof casing, the plurality of layers comprising a thermoplastic material or a coating comprising thermoplastic material;
    positioning the plurality of layers on top of one another within an initial mold while in the gas-proof casing;
    positioning at least one converter between the plurality of layers;
    creating a vacuum in the gas-proof casing;
    pressing the plurality of layers into the initial mold to deform the plurality of layers to match the shape of the initial mold;
    applying heat to the plurality of layers in the deformed state with the at least one converter to only partially join together the plurality of layers;
    subsequently cooling down the plurality of layers;
    after cooling the plurality of layers, heating the plurality of layers to permanently join the plurality of layers;
    cooling the plurality of layers to produce the orthopedic device.

* * * * *